(12) United States Patent
Lehmann et al.

(10) Patent No.: US 6,306,428 B1
(45) Date of Patent: Oct. 23, 2001

(54) TIME-RELEASE LAMINAR PHARMACEUTICAL COMPOSITION

(75) Inventors: Klaus Lehmann, Rossdorf; Hans-Ulrich Petereit, Darmstadt, both of (DE)

(73) Assignee: Roehm GmbH Chemische Fabrik, Darmstadt (DE)

( * ) Notice: Subject to any disclaimer, the term of this patent is extended or adjusted under 35 U.S.C. 154(b) by 0 days.

(21) Appl. No.: 09/058,951

(22) Filed: Apr. 13, 1998

(30) Foreign Application Priority Data

Apr. 16, 1997 (DE) ............................................. 197 15 794

(51) Int. Cl.⁷ ....................................................... A61K 9/00
(52) U.S. Cl. ................................................................ 424/438
(58) Field of Search ............................................... 424/438

(56) References Cited

U.S. PATENT DOCUMENTS

| | | | |
|---|---|---|---|
| 3,295,246 | * | 1/1967 | Landsman et al. . |
| 3,625,214 | | 12/1971 | Higuchi . |
| 4,228,149 | * | 10/1980 | Brewer . |
| 4,601,893 | * | 7/1986 | Cardinal . |
| 4,705,695 | | 11/1987 | Lehmann et al. . |
| 4,861,596 | * | 8/1989 | Curtis . |
| 4,990,381 | * | 2/1991 | Holzner . |
| 5,141,810 | * | 8/1992 | Ranade . |
| 5,705,189 | | 1/1998 | Lehmann et al. . |
| 5,776,481 | * | 7/1998 | Karst et al. . |

FOREIGN PATENT DOCUMENTS 26 56 387   6/1977   (DE) .

* cited by examiner

Primary Examiner—Raj Bawa
(74) Attorney, Agent, or Firm—Oblon, Spivak, McClelland, Maier & Neustadt, P.C.

(57) ABSTRACT

A time-release laminar pharmaceutical composition, comprised of rolled or folded layers of a polymer film, that contain a pharmaceutically active substance, in which the outer surface area of the polymer film which contains the active substance, and which is accessible to the digestive juices, amounts to at most 25% of the entire surface area in the rolled or folded state, and the rolled or folded layers adhere to one another in such a way that the laminar form of medication maintains its rolled or folded form for a period of at least one hour in the release test according to USP 23, Method A, apparatus 2, at 37° C. and 50 rpm, in artificial gastric juice, and at least 30% of the active substance contained in it is released in the rolled or folded state.

12 Claims, 2 Drawing Sheets

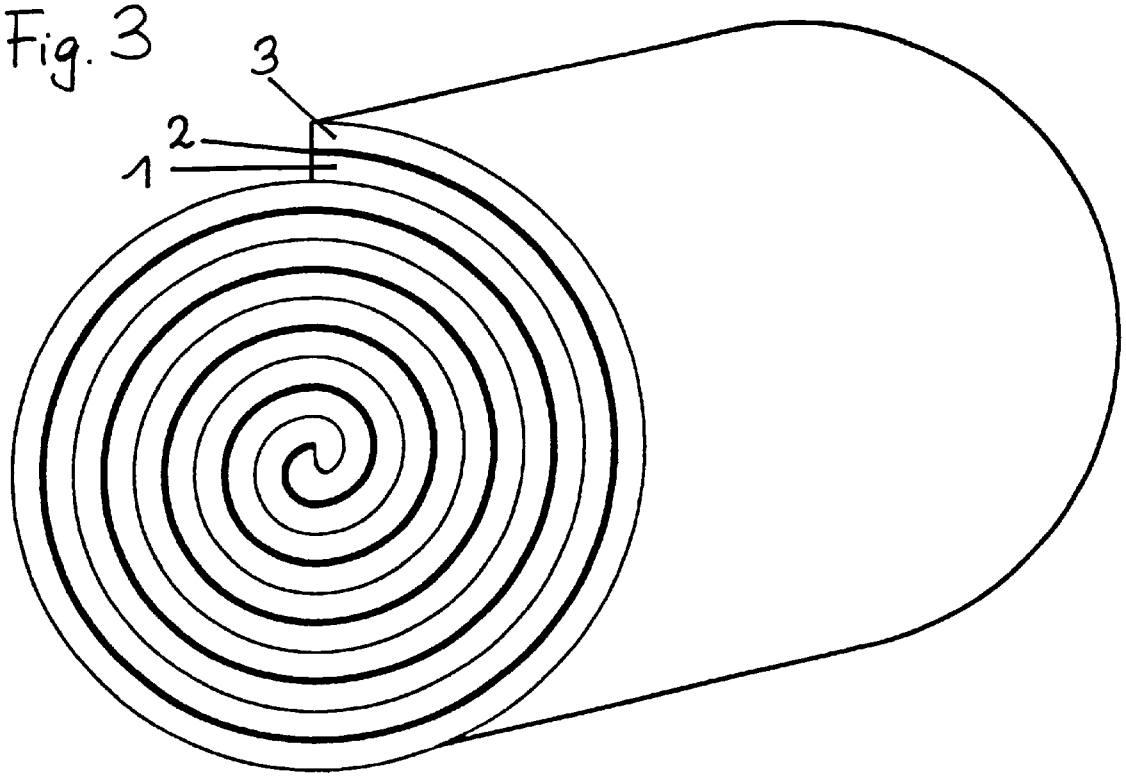

TIME-RELEASE LAMINAR PHARMACEUTICAL COMPOSITION

FIELD OF THE INVENTION

Figure 1:
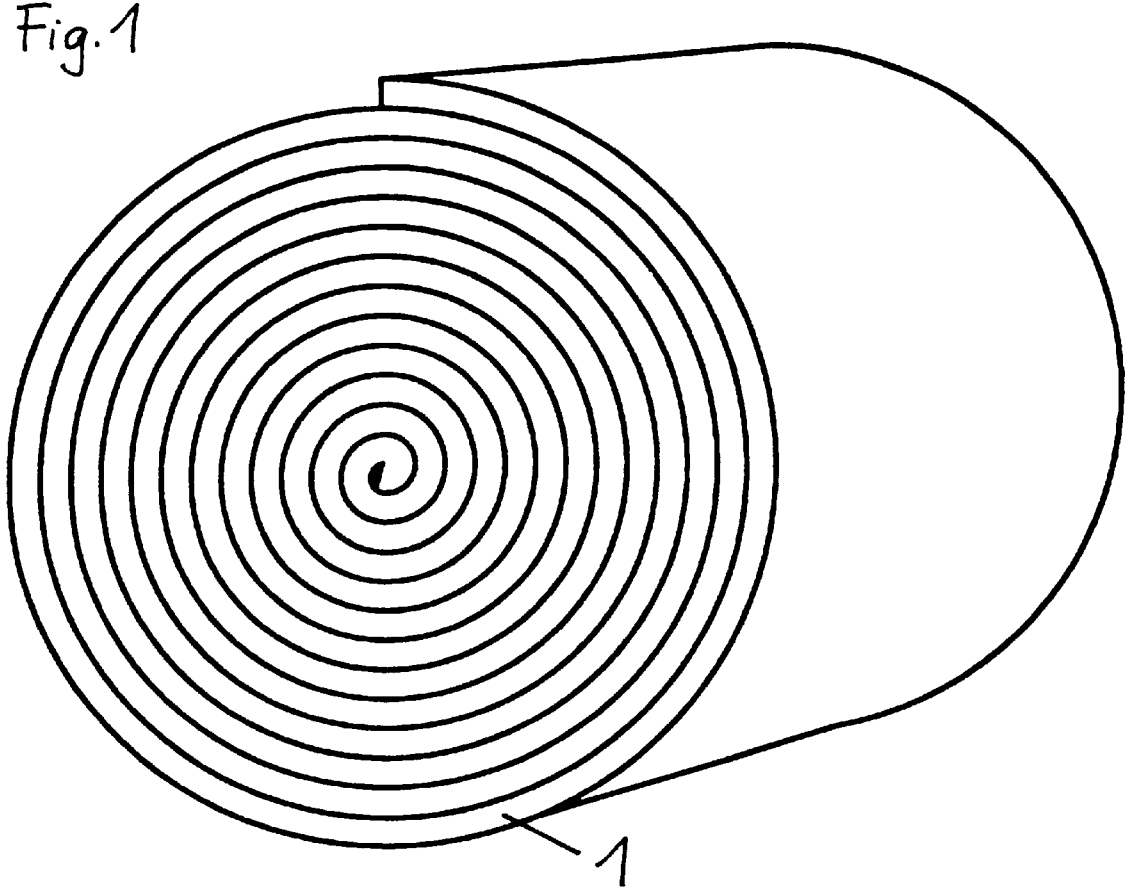

The invention relates to laminar forms of medication made from rolled or folded polymer films which contain an active substance.

BACKGROUND OF THE INVENTION

Rolling-up polymer films which contain active substances, to produce forms of medication, is known. EP 0 209 212, EP 0 086 997, and EP 0 122 574 describe embedding active substances in polymer films for delayed release. These films are processed individually or in comminuted form into capsules, or compressed into tablets. Delayed release is essentially determined by the type of film and by the size of its surface area. At the beginning of active substance release, the entire film surface is soon in contact with the digestive fluids, and therefore is available to release the active substance.

EP-A 010 987 describes rolling-up a film which contains an active substance, for the administration of veterinary medications to ruminants, where the primary form is supposed to unroll after administration and expand to form an enlarged secondary form. The purpose of the volume expansion is so that the medication remains in the rumen for a longer time. The release of the active substance then also takes place from the entire surface area of the film, which is accessible to the digestive juices. A laminate which is produced with a pressure-sensitive adhesive, in accordance with EP-A 363 187, is also supposed to act in a similar manner. This is also described in EP-A 350 188.

It has also been proposed to introduce rolled-up films which contain active substances into body cavities, e.g., EP-A 447 719, specifically for therapy of middle-ear infections, or, according to JP-Abstract 82-90967 (Derwent), intravaginally for administration of spermicides as a contraceptive. In these cases, only local release of active substance is intended, and here again, one can assume that the film roll will soon expand because it absorbs moisture, and that the active substance will be released from the loosened film laminate.

A form of medication which floats in the stomach is described in EP-A 326 816. Here, polymer films enriched with the active substance are processed to produce various shapes, which are supposed to have an extended dwell time in the stomach because of the use of porous materials in them, along with other materials, or inclusion of air. As a further development of this idea, DE 4419818 mentions rolled films which remain in the stomach for an extended period of time because they unfold, and are intended to pass through the pylorus passage only with difficulty because of their size, which is greater than 5 cm². Here again, the entire surface area of the film becomes available for active substance release after the film has unfolded or expanded.

SUMMARY OF THE INVENTION

An object of the present invention to make available a time-release pharmaceutical composition comprising: a core which contains an active substance, and a film sheath, or a sponge-like matrix structure. Controlled active substance release is accomplished with rolled or folded layers of a polymer film, that contain a pharmaceutically active substance, in which the outer surface area of the polymer film which contains the active substance, and which is accessible to the digestive juices, amounts to at most 25% of its entire surface area in the rolled or folded state, and that the rolled or folded layers adhere to one another in such a way that the laminar form of medication maintains its rolled or folded form for a period of at least one hour in the release test according to USP 23, Method A, apparatus 2, at 37° C. and 50 rpm, in artificial gastric juice, and that at least 30% of the active substance contained in it is released in the rolled or folded state.

BRIEF DESCRIPTION OF THE INVENTION

The invention will be explained with the figures below, but is not restricted to the embodiments shown.

FIG. 1: Schematic view of a laminar form of medication made from a rolled polymer film which contains active substance (1).

Figure 2:
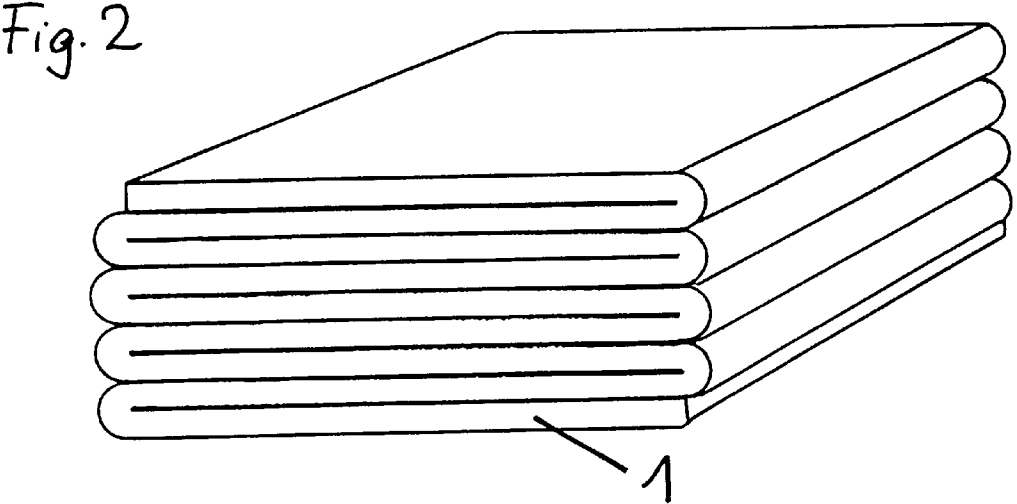

FIG. 2: Schematic view of a laminar form of medication made from a folded polymer film which contains active substance (1).

FIG. 3: Schematic view of a rolled laminar form of medication with a polymer film which contains active substance (1), an adhesive layer (2), and an intermediate layer (3).

DETAILED DESCRIPTION OF THE INVENTION

The principle of the invention lies in that a very uniform vehicle is made from the laminar structure, with only a small surface area of the polymer film containing the active substance having contact with the digestive fluids. The laminar structure results in diffusion of the active substance into the digestive fluid essentially only at the cut edges and from the layers, and from within them via an extended diffusion path, while no or little diffusion takes place between the layers. The diffusion of active substance therefore follows the laminar structure, which makes it possible to adjust the delayed, controlled release of the active substance in a reproducible manner.

In a preferred embodiment, the polymer film which contains the active substance is provided with another one or two layers before being rolled—or folded—up. The additional layer can act as an intermediate layer ((3), see FIG. 3), to reduce or prevent diffusion between the layers containing active substance, and thereby contribute to the controlled release of active substance. Also, another layer can additionally exert an adhesive function ((2), see FIG. 3), which contributes to holding the laminar medication together over an extended period of time in the presence of the digestive fluids, if the polymer films do not naturally adhere to each other sufficiently under the conditions of being rolled or folded together.

Another inventive development consists of providing the laminar form of medication with a band, which on the one hand contributes to holding the laminar form of medication together, and on the other hand prevents the diffusion of active substance from the outermost polymer film layer, to a great extent.

As compared with conventional forms of timed-release medication with a core containing the active substance and a film sheath which controls the release of active substance, there is the advantage of having a simpler, very uniform structure, and easier production, according to the efficient processes of film manufacturing by means of coating, extrusion, and "hot melt" processes, which have been well developed in recent years, and as they are increasingly being used in the production of transdermal forms of medication. The core can be completely eliminated. Likewise, no complicated and critical coating processes are required.

Polymer films suitable for the invention are rollable or foldable films with a slight thickness, made from synthetic, semisynthetic, or natural polymers, e.g., from a plastic or a chemically modified natural substance, such as a cellulose ether or ester, for example, or on the basis of paper or protein (e.g. casein, gelatin, or derivatives). The film can also consist of a mixture of different polymers.

The laminar structure maintains its rolled or folded form in the presence of digestive fluid, gastric and/or intestinal juices over an extended period of time. An extended period of time is understood to mean that unrolling or unfolding is only supposed to take place once the main amount of the active substance contained has essentially already been released via the laminar layers of the outermost surface area.

This time condition depends on the intended therapeutic use. A rough guideline for the stated extended period of time is not shorter than the stomach passage time of approximately 1–2 hours, which holds true for normal food consumption. In general, more than 30% of the active substance contained is to be released during the extended period of tine during which the rolled or folded form is maintained. Preferably, however, the extended period of time lies within the range of 3–6 hours or more, and the amount of active substance which is essentially released in "laminar" manner is at least 50%, particularly at least 60%.

These in vivo conditions can be considered to have been met if the laminar form of the medication maintains its rolled or folded form for a period of at least one hour, preferably at least two hours, in the in vitro release test according to USP 23 (1994, p. 1795 ff.), Method A, apparatus 2 ("Paddle", see p. 1792), at 37° C. and 50 rpm, in artificial gastric juice (0.1 M HCl), and that at least 30%, preferably at least 50%, more preferably at least 60% of the active substance contained in it is released while in the rolled or folded state.

In no event is the laminar form of medication allowed to unroll or unfold immediately after being taken, since then the principle of delayed and controlled release of active substance would not be sufficiently met (and could also be achieved with simple forms of medication corresponding to the state of the art). Depending on the therapeutical use, it can be desirable that the release of active substance at first take place essentially in "laminar" manner over an extended period of time, but then the remaining amount of active substance is released as the laminar form unrolls or dissolves.

Suitable polymers for producing the laminar pharmaceutical composition can be selected very generally, in accordance with whether they are available or can be manufactured in film form, and have sufficient flexibility so as not to break or tear when rolled or folded. Of course the polymer material must be suitable for pharmaceutical purposes and possess sufficient absorption capacity for the active substance. Pre-finished films that can be mentioned are films of paper or polyvinyl acetate, for example. A number of additional polymeric materials are available as solids, for example as granulate, or in the form of solutions or dispersions, which can be converted into films by the coating of carrier films, extrusion, or "hot melt" processes (see in this regard EP-A 704 207, EP-A 704 208, EP-A 727 205, or EP-A 704 205, for example).

Preferably, polymer materials which eventually dissolve or decompose under the conditions of the digestive tract are used. For this purpose, polymers which have proven themselves for coating forms of medication can be used. These include poly(meth)acrylates which dissolve in gastric juices, for example copolymers of 25 wt.-% methyl methacrylate, 25 wt.-% butyl methacrylate, and 50 wt.-% dimethylaminoethyl methacrylate (type EUDRAGIT® E 100), which are soluble in the digestive tract below pH 5, and bulk up and are permeable above pH 5. Furthermore, copolymers of methacrylic acid which are resistant to gastric juices but dissolve in intestinal juices, for example copolymers of 50 wt.-% ethyl acrylate or methyl methacrylate and 50 wt.-% methacrylic acid (EUDRAGIT® L/S types) should be mentioned. Likewise, bulking polymethacrylates based on copolymers of 2-trimethyl ammonium methyl methacrylate are possible. Here, polymers of 30 wt.-% ethyl acrylate, 5 or 10 wt.-% 2-trimethyl ammonium methyl methacrylate, and a residual portion of methyl methacrylate (EUDRAGIT® RS, EUDRAGIT® RL) can be mentioned. Furthermore, copolymers of methyl acrylate, methyl methacrylate, and methacrylic acid are suitable (see, for example, EP-A 704 207, EP-A 704 208).

In addition, cellulose derivatives with similar properties, such as cellulose acetate phthalate, hydroxypropyl methylcellulose phthalate, carboxymethylcellulose, and similar compounds which are soluble in the intestinal tract above pH 5, can also be used, as can polyvinyl acetate phthalate. However, the film layers can also contain polymers which bulk up in water and are soluble in water, such as cellulose, cellulose ether (methylcellulose, hydroxypropyl methylcellulose, and similar derivatives), as well as polyvinyl alcohol and mixed polyvinyl alcohol, polyvinyl acetate compounds with graduated ability to bulk up or dissolve in water. Also, starch (solubilized starch capable of extrusion), gelatin, coliagen, casein and derivatives are suitable, if necessary formulated with the addition of plasticizers and binders in such a way that they form sufficiently stable film layers.

To make the form of medication according to the invention available, the preparation of a polymer film which contains an active substance is first required. This can be done in a known manner. The polymers can be present, for example, in organic solution or in aqueous dispersion. The active substance can be added to the mixture directly, if necessary with additional processing aids, such as plasticizers. The suspension or solution containing the active substance can be distributed in a thin layer and form a thin film with a thickness of 0.03 to 1 mm, for example, preferably in the range of 0.1 to 0.5 mm, after evaporation of the solvent. In this connection, as a guideline, the layer thicknesses of thin polymer films, in the range below approximately 0.15 mm, should vary by not more than +/−25%, and in the case of thicker films by not more than approximately +/−10%.

If cellulose in paper form is used as the polymer film, the paper can be saturated with an aqueous solution of the active substance, for example, and the active substance can be fixed in place in the paper by drying. The paper/polymer film can be provided with an adhesive layer and fundamentally be converted to the laminar form of medication by folding or rolling, in the same way as a polymer film made from a poly(meth)acrylate.

As an alternative, a polymer film which contains an active substance can also be obtained without using a solvent, from a polymer melt, using the so-called "hot melt" process, where the polymer, if necessary containing flow improvement agents, for example waxes, cetyl alcohol, etc., is liquefied at a temperature above its glass temperature, and spread out or extruded as a thin film (see in this regard EP-A 727 205, EP-A 704 205). In the simplest case, the film containing the active substance can be rolled up or folded to produce a laminar form of medication. This presupposes that the polymer film which contains the active substance demonstrates sufficient adhesion to itself, so that premature unfolding or unrolling does not occur in the presence of the digestive fluids. A suitable polymer for this purpose is a copolymerizate of ethyl acrylate and methyl methacrylate in a ratio of 2:1 (EUDRAGIT® NE).

In the simplest form of this laminar form of medication, it must be taken into consideration that while the diffusion of the active substance takes place essentially in a laminar manner, in other words, along the inner layers, direct diffusion via the surface area of the outermost layer of the last winding also takes place, and that a certain portion of the active substance on the inside diffuses through from layer to layer. This effect, which is sometimes undesirable, is, of course, dependent on the number of layers and their packing density, the polymer used, and the active substance used. In many cases, however, this effect will be sufficiently slight to be ignored or insignificant.

If diffusion via the outermost layer, which lies on the surface, or diffusion between the layers which contain the active substance is supposed to be reduced, one or two additional layers can be applied on one or both sides of the polymer film which contains the active substance. These layers can exert the function of an intermediate or separating layer for the layers which contain the active substance, or can also have the function of an adhesive layer which produces or supports cohesiveness of the laminar form of medication over an extended period of time, in the presence of the digestive fluid.

In the production of the laminar form of medication, the polymer film which contains the active substance is generally first folded or rolled over its entire production width. This is supposed to happen in such a way that the layers have intimate contact with one another, under slight pressure, for example. Afterwards, the roll or folded stack obtained, which can have a diameter, i.e. a height, of approximately 0.5 to 5 cm, preferably from approximately 2–4 cm, is cut into many slice-like individual portions. The width of the finished laminar form of medication can lie in the range of 0.5–2 cm, for example. What determines the speed of active substance release, to a significant extent, is the surface area ratio of the cut edges to the inner film surface area.

In order to make the desired release speed possible, it is necessary that the outermost surface area of the polymer film that contains active substance, and which is accessible to the digestive juices, amounts to at most 25%, preferably at most 5%, of the surface area of the polymer film in the rolled or folded state. A reduction of the surface area results from the ratio of the layer thickness of the polymer film to its number of windings or folds and their size (diameter of the roll or height of the folded stack). The rolled or folded layers must adhere to one another in such a way that the laminar form of medication maintains its rolled or folded form over an extended period of time in the presence of digestive fluids, so that the active substance is essentially released only in a "laminar" manner via the outer surface area of the cut edges.

If the adhesion of the laminate to itself is not sufficient, or if the laminate is to be additionally stabilized without an adhesive layer in a simple manner, the roll or the folded stack can also be secured with a band which runs around the outside and is fixed securely in place. A possible material which can be used for this purpose is a methacrylate copolymer or a film strip provided with an adhesive layer.

In a further development of the invention, the polymer film which contains the active substance can be provided with one or more additional layers before being folded or rolled up. These can fulfill the function of an adhesive layer and/or a layer to regulate the release of active substance. Also, the additional layer can be used to control later decomposition of the laminar form of medication, if necessary.

Another layer can be used to delay or regulate the release of active substance from the layer which contains the active substance, i.e., an intermediate layer. If, for example, it is highly hydrophobic, the penetration of dissolved hydrophilic active substance is made more difficult. If the intermediate layer is hydrophilic, bulks up in water, or is actually soluble in water, the release of the active substance is accelerated, going as far as complete decomposition or dissolution of the medication vehicle as a whole. Suitable intermediate layers can also consist of pre-finished films, for example, cellulose acetate, polyvinyl acetate, polyvinyl alcohol, or polyethylene, with the polymer layer which contains the active substance being applied to them.

Another layer, for example, can be an adhesive layer that causes or at least supports cohesion of the laminar composition, for example if the adhesion of the polymer film containing the active substance to itself, or to another intermediate layer, is not sufficient. Suitable adhesive layers can consist of dimethyl polysiloxane or butyl acrylate and ethyl hexyl acrylate copolymers. Other suitable adhesive layers are derived from compositions for skin adhesives or transdermal patches (see EP-A 315 218, EP-A 617 972, for example). EP-A 415 055 describes a skin adhesive made from cationic (meth)acrylate copolymers, for example, which are formulated with an organic carboxylic acid, such as adipinic acid or laurinic acid.

A rolled laminar form of medication can be produced by hand in the pharmacy, for example, from a polymer film which contains the active substance, and can also have an intermediate layer and/or an adhesive layer. For this purpose, the film, which can measure 50×50 cm with a thickness of 0.2 mm, can be rolled up on a flat surface using a flat plate pushed over it from the top, under slight pressure, so that a roll with a width of 50 cm and a diameter of 0.2 to 1 cm is obtained. Then pieces with a width of 0.5–1 cm, for example, can be cut off.

On an industrial scale, rolling methods are used in multiple ways for the production and packaging of films. In the production of small capacitors, films are also converted to small rolls with a high level of precision. Such known rolling methods and devices suitable for them, can be adapted to or designed for the laminar forms of medication of this invention, so that the rolling process and cutting of the roll can be done by machine. In a similar manner, folded laminar forms of medication can also be produced by hand or by machine.

If necessary, the cohesion of the laminar form of medication can be improved in that cutting of the portions takes place using a hot wire or knife, or even using a laser beam, so that the polymer is slightly sintered at the cut edges. If a band is provided, this can also be applied by hand or by machine.

The following examples serve to illustrate the invention.

EXAMPLES

Example 1

3 grams theophylline powder are stirred into 30 g of an aqueous plastic dispersion. The plastic dispersion contains 9 g of a copolymerizate of 65 weight-% methyl acrylate, 25 weight-% methyl methacrylate, and 10 weight-% methacrylic acid. In addition, 0.45 g triethyl citrate as a plasticizer and 12 g water are added to the mixture. It is stirred for another 5 minutes, and the mixture is then placed in a trough with a surface area of 16×16 cm, lined with polyethylene film, and dried at 50° C. until complete film formation has taken place, so that a film with a thickness of approximately 0.5 mm is formed.

From the film, strips with a width of 2.5 cm and a length of 10 cm are cut and a foam film with a thickness of 1 mm coated with adhesive on both sides is pressed onto them. The combined films are now rolled up, under slight pressure, into little rolls with a width of 2.5 cm and a diameter of about 12 mm, and finally a band of Tesa adhesive tape, coated on one side, is glued around them to fix them in place.

From the little roll, little slices with a thickness of 6 mm are cut off with a sharp knife, and these slices are taken in this form, as a time-release medication. One little slice contains 72 mg theophylline and releases 10% of the active substance after 3 hours, 58% after 6 hours, and 85% after 9 hours, in an in vitro release test according to LISP (paddle apparatus) at 100 revolutions/minute and 37° C., in phosphate buffer, pH 7.5.

Example 2

A suspension of 3 g theophylline is produced analogously to Example 1, and 30 g of the plastic dispersions indicated there, together with 0.45 triethyl citrate as a plasticizer and 12 g water as a solvent, are stirred for another 5 min, but then drawn out with a doctor blade with a slit opening of 500 µm, so that after five hours of drying at 50° C., a film with a layer thickness of approximately 200 µm is obtained. On this film, an adhesive solution of dimethyl polysiloxane in trichlorofluoroethylene (Medical Adhesive Dow Corning 355) was applied in a layer of approximately 50 µm. After approximately 30 min at room temperature, the adhesive layer has dried on, and the film is now cut as strips with a width of 2.5 cm and a length of approximately 30 cm. After it is rolled up, little oval slices are cut off using a sharp knife, under slight pressure, these slices having the shape of an ellipsis with the diameters 5 and 10 mm when seen from the top. The slice thickness was 2.5 mm and they contained 24.3 mg active substance per dose unit. In the release test according to USP, using the paddle method at 100 rpm and 37° C., a release of active substance of 9% after 1 hour was found in artificial gastric juice; after a switch to artificial intestinal juice (phosphate buffer pH 7.5) and stirring for another 5 hours, 39% of the active substance had been released, and after 24 hours, 83%. Slices with a thickness of 5.0 mm contained 50 mg active substance and demonstrated 5% active substance release in the same test, after 1 hour in artificial gastric juice, and 23% after another 5 hours in phosphate buffer pH 7.5, 60% after 24 hours. Finally, the film roll dissolved to a great extent.

Example 3

600 Mg of bisacodyl was suspended in 12 g water, mixed with 30 g of an aqueous dispersion of EUDRAGIT® NE 30 D (containing 9 g copolymer of ethyl acrylate and methyl methacrylate 2:1). From this, a film with a thickness of 0.2 mm was produced by drying at 50° C., on a surface area of 14×20 cm. From this, a strip with a length of 14 cm and a width of 5 cm was cut and alternately folded in layers of 12 mm each (=L), until a height of 2.5 mm (=H) was obtained (see the folding principle in FIG. 2). The films adhered to one another without additional adhesive additive. The last 3 cm of the film, at the end, were passed around the laminate as a band. From the laminate, which had a total width of 5 cm, pieces with a width of 1 cm (=B) were now cut off, so that the following dimensions are obtained for the form of medication: L=12 mm, B=10 mm, and H=2.5 mm. The weight of the little laminate pieces was between 295 and 325 mg and they contained 20 mg active substance each. In the release test in artificial gastric juice, using the USP paddle device, 18% of the active substance was released after 1 hour, 29 after 3 hours, 40 after 8 hours, and more than 80 after 24 hours.

Example 4

600 Mg of phenyl propanolamine hydrochloride was dissolved in 12 g water and mixed with 30 g of an aqueous dispersion, containing 9 g copolymer of ethyl acrylate and methyl methacrylate 2:1. A film strip dried at 50° C. with a length of 15 cm, a width of 4 cm, and a thickness of 0.2 mm, was coated with 2 ml adhesive solution on the basis of dimethyl polysiloxane (Dow Medical Adhesive) and again divided lengthwise, so that a film strip with a width of 2 cm and a total length of 30 cm was obtained. The films were rolled up one after the other, so that a roll diameter of 9 mm was obtained. Slices with a thickness of 4.3 to 5 mm were now cut off with a sharp knife, which had a weight of 302 to 316 mg and contained 19.0 to 20.0 mg active substance. The active substance was continuously released in the release test according to USP—as described in the above examples—and had been practically completely released within 6 hours.

Example 5

3 Grams of phenyl propanolamine hydrochloride were dissolved in 12 g water and applied to a nonwoven paper with a surface area of 18×18 cm and a thickness of 0.1 mm. Here, the paper absorbs 9 g of the solution, corresponding to 2 g phenyl propanolamine. The paper was dried at 50° C. for 90 minutes, and glued onto a polyethylene film with a thickness of 0.1 mm and the same area, using the adhesive mentioned in Example 4. Adhesive was again applied to the paper layer containing active substance, and then this laminated film was rolled up. The roll, with a width of 5 cm, has a cylindrical cavity on the inside with a diameter of 2 mm, and a total diameter of 10 mm. Slices with thickness of 10 mm were cut out and contain 80 mg active substance per dose unit.

Example 6

150 Grams of a 30% dispersion of a copolymerizate of 30 wt.-% ethyl acrylate, 65 wt.-% methyl methacrylate, and 5 wt.-% trimethyl ammonium methyl methacrylate chloride (EUDRAGIT® RS 30 D) are mixed with a pre-mixture of 9 g triethyl citrate as a plasticizer and 3.5 g polysorbate 80 as a stabilizer, in 6.5 g water, and stirred for 5 min. Now 3 g polyvinyl alcohol were slowly added as a fine-grain granulate, while stirring, and stirring continued for another 3 h. The viscous dispersion was passed through a sieve with a clear mesh width of 0.1 mm, and applied to a polyethylene film (HostaphanS, type 931/8478, Renken GmbH) in a film drawing device (Mathes, type LTF 142691), in a layer thickness of 400 µm, over a surface area of approximately 20×20 cm, with approximately 30 ml of liquid being used for this purpose. After drying for 30 minutes at 80° C., a clear film with a layer thickness of approximately 105 µm is formed, which can be used as an intermediate layer with the films containing active substance in Examples 2 and 4.

The priority document, German Patent Application 19715794.7 dated Apr. 16, 1997, is incorporated herein by reference.

Obviously, numerous modifications of the invention are possible in light of the above teachings. Within the scope of the appended claims, the invention may be practiced in a manner other than that specifically given above.

What is claimed is:

1. A laminar time-release pharmaceufical composition comprising:

a polymer film containing a pharmaceutically active agent absorbed therein, wherein the polymer film is rolled or folded to form a laminar structure in which the rolled or folded layers of the polymer film adhere to one another and form successive layers of the laminar structure, and the area of the outer surface of the laminar structure is at most 25% of the surface area of the polymer film, and the rolled or folded layers adhere to one another so that the laminar structure does not unroll or unfold for a period of at least one hour during a release test according to USP 23, Method A, apparatus 2, at 37° C. and 50 rpm, in artificial gastric juice, and at least 30% of the active agent is released before the laminar structure unrolls or unfolds, and the laminar time-release pharmaceutical composition dissolves or decomposes under the conditions of the digestive tract.

2. The lainiar composition according to claim 1, which further comprises a layer selected from the group consisting of an adhesive layer, an intermediate layer, and combinations thereof.

3. The laminar composition according to claim 1, which is surrounded by a band.

4. The laminar composition of claim 1, wherein the polymer film that contains an active agent is at least one polymer selected from the goup consisting of a (meth) acrylate copolymer, cellulose acetate phthalate, hydroxypropyl methylcellulose phthalate, carboxymethylcellulose, polyvinyl acetate phthalate, methylcellulose, hydroxypropyl methylcellulose, polyvinyl alcohol, mixed polyvinyl alcohol, or polyvinyl acetate compounds, optionally with additives of plasticizers or binders.

5. The laminar composition of claim 1, wherein the polymer film is at least one polymer selected from the group consisting of cellulose, cellulose ethers, methylcellulose, hydroxypropyl methylcellulose, starch, solublized starch gelatin, collagen, and casein.

6. The laminar composition of claim 2, wherein said adhesive layer is selected from the group consisting of dimethyl polysiloxane, an acrylatc adhesive, and an adhesive based on natural substances.

7. A procoss for the production of the laminar time-release pharmaceutical composition of claim 1 comprising:

rolling or folding the polymer film containing a pharmaceutically active agent absorbed therein, and a optional layer selected from the group consisting of an intermediate layer, an adhesive layer and combinations thereof, and cutting said polymer film, wherein said laminar time release pharmaceutical composition dissolves or decomposes under the conditions of the digestive tract.

8. The process of claim 7 wherein the outer surface of the polymer film that contains the active agent, and which is accessible to digestive juices, amounts to at most 25% of the entire surface area in the rolled or folded state.

9. The laminar composition of claim 1, wherein the polymer film comprises at least one member selected from the group consisting of polymethacrylates, copolymers of 2-trimethylammonium methylmethacrylate, copolymers of methylacrylate, copolymers of methylmethacrylate, cellulose, and cellulose ethers.

10. The laminar composition of claim 2, wherein said adhesive layer comprises at least one member of the group consisting of dimethylpolysiloxane copolymers, butylacrylate copolymers, ethylhexylacrylate copolymers, and cationic methacrylate copolymers.

11. The laminar composition of claim 2, wherein said intermediate layer comprises at least one member of the group consisting of cellulose acetate, polyvinyl acetate, polyvinyl alcohol, and polyethylene.

12. The laminar composition of claim 1, further comprising a plasticizer or binder.

* * * * *